United States Patent [19]

Verkaart

[11] Patent Number: 4,900,308
[45] Date of Patent: Feb. 13, 1990

[54] GAS ELIMINATION DEVICE

[75] Inventor: Wesley H. Verkaart, Duxbury, Mass.

[73] Assignee: Level 1 Technologies, Inc., Marshfield, Mass.

[21] Appl. No.: 235,964

[22] Filed: Aug. 23, 1988

Related U.S. Application Data

[63] Continuation of Ser. No. 54,979, May 27, 1987, abandoned.

[51] Int. Cl.[4] .............................................. A61M 5/14
[52] U.S. Cl. ..................................... 604/126; 604/406
[58] Field of Search ............... 604/122, 126, 190, 406, 604/80–85, 246, 252; 55/159

[56] References Cited

U.S. PATENT DOCUMENTS

| | | | |
|---|---|---|---|
| 2,758,597 | 8/1956 | Elder | 604/80 |
| 3,677,248 | 7/1972 | McPhee | 604/126 |
| 3,967,620 | 7/1976 | Noiles | 604/126 |
| 4,030,495 | 6/1977 | Virag | 604/126 |
| 4,083,706 | 4/1978 | Wiley | 604/190 |
| 4,198,971 | 4/1980 | Noiles | 604/126 |
| 4,227,525 | 10/1980 | Lundquist | 604/126 |
| 4,256,105 | 3/1981 | Leahey et al. | 604/126 |
| 4,447,230 | 5/1984 | Gula et al. | 604/126 |
| 4,534,757 | 8/1985 | Geller | 604/126 |
| 4,623,333 | 11/1986 | Fried | 604/80 |
| 4,643,713 | 2/1987 | Viitala | 55/159 X |
| 4,650,458 | 3/1987 | Dahlberg et al. | 604/126 |
| 4,664,800 | 5/1987 | Raines et al. | 604/126 |

*Primary Examiner*—Dalton L. Truluck
*Assistant Examiner*—Denise W. DeFranco
*Attorney, Agent, or Firm*—Berman, Aisenberg & Platt

[57] ABSTRACT

An air elimination device includes a plenum arranged to cause a reduction in flow velocity of a physiological fluid whereby air bubbles form and rise to the top of the plenum. A hydrophobic membrane covers the top of the plenum, and the pressure in the fluid is greater than that which is required to drive the released air through the membrane and into the atmosphere. The air which collects at the top of the plenum forms a protective surface on the bottom of the hydrophobic membrane to prevent its being clogged by cellular materials. A support stand engages the air eliminator to hold it in the desired orientation whereby the air bubbles form at the top of the plenum.

15 Claims, 2 Drawing Sheets

GAS ELIMINATION DEVICE

This is a continuation of application Ser. No. 054,979, which was filed on May 27, 1987, and is now abandoned.

TECHNICAL FIELD

This invention relates to the art of elimination of air or other gasses from physiological fluids.

BACKGROUND ART

When administering physiological fluids to a patient, it is desirable to remove excess air or other gasses prior to introduction of the fluids into the patient.

Devices are known which eliminate gasses from fluids to be applied to a patient. For example, U.S. Pat. No. 4,190,426 (Ruschke) teaches a gas separating and venting filter wherein gas is removed from a fluid by a liquid-wetting (hydrophilic) membrane which divides the device into inlet and outlet chambers. The inlet chamber includes a liquid-repellent (hydrophobic) membrane which passes gas removed by the liquid-wetting filter to the atmosphere.

U.S. Pat. No. 4,413,990 (Mittleman) and U.S. Pat. No. 4,571,244 (Knighton) teach devices which also rely upon liquid-wetting filters to remove gasses. In the Mittleman device, a membrane valve is placed at the bottom of a burette for removing gasses. The Knighton apparatus includes a horizontally disposed cylinder having a liquid-wetting filter at one end and a liquid-repellent filter at an opposite end. The fluid to be treated is introduced at a mid-point of the cylinder.

U.S. Pat. No. 4,572,724 (Rosenberg et al.) teaches a blood filter for use in a cardiopulmonary by-pass system. An upper chamber is arranged to receive blood and cause it to flow in a circular direction whereby air is separated by the centrifugal forces on the blood. Air bubbles above a predetermined size which were not removed in the first chamber are removed by a cylindrical filter made of a pleated screen.

SUMMARY OF THE INVENTION

Air elimination devices which rely upon a hydrophilic filter for removal of air are generally not useful for treatment of blood because the filters have pore sizes which are too small to pass red blood cells. Systems not relying on a hydrophylic filter, such as the one shown by Rosenberg, are quite complicated and are expensive to manufacture.

In accordance with the invention, a simple, inexpensive apparatus is provided which takes advantage of natural phenomena to efficiently eliminate air or other gasses from a physiological fluid being administered to a patient. The device is useful for a wide variety of physiological fluids, including blood. One preferred use for the air elimination device of the invention is in series with an apparatus which heats blood being administered to a patient, the air elimination device removing gasses which normally accompany the heating process.

The eliminator of the invention includes a vertically-oriented column configured to provide a downward flow velocity for a fluid which is less than the rate at which a bubble of gas to be removed will rise through the fluid. The bubbles form and rise through the fluid to the top of a velocity-reducing plenum, and a liquid-repellent membrane covers the upper end of the plenum. Air bubbles collect on the lower surface of the liquid-repellent membrane, and the air then passes through the membrane into the atmosphere.

In a preferred embodiment, a one-way valve is placed above the membrane to exhaust gas which has passed through the membrane to the atmosphere while preventing the flow of gas in a reverse direction. The one-way valve is a safety measure and is not required if the patient is necessarily located either above or level with the gas-eliminating device.

Because the elimination device of the invention relies upon natural forces to remove gas from the fluid, a liquid-wetting filter as used in the prior art is not required, and the device may be used with a wide variety of fluids including blood. If it is desired to ensure that particulates are removed, a filter screen may be placed in the flow, but this is not necessary in many instances.

The inlet, outlet, and plenum are configured so that for a pre-determined pressure difference, the flow rate of the liquid in the plenum will be reduced to a rate at which gas bubbles will form and rise to the top of the plenum through buoyancy forces.

As will be appreciated from the description below, the invention is orientation sensitive, and in a preferred embodiment, the gas-elimination device is in combination with a support stand which provides a bracket engaging the air-elimination device in such a manner that it is necessarily in the proper orientation. The stand may also provide supports for the containers of physiological fluids to produce a desired pressure head.

An object of this invention is to provide a device for eliminating gas from a fluid, whereby bubbles which are introduced with the fluid or form naturally in the fluid rise to the top of a plenum.

Another object of this invention is to provide an arrangement for eliminating gas from a fluid whereby an air elimination apparatus is held by a support stand in a pre-determined orientation.

DETAILED DESCRIPTION OF THE INVENTION

Figure 1:
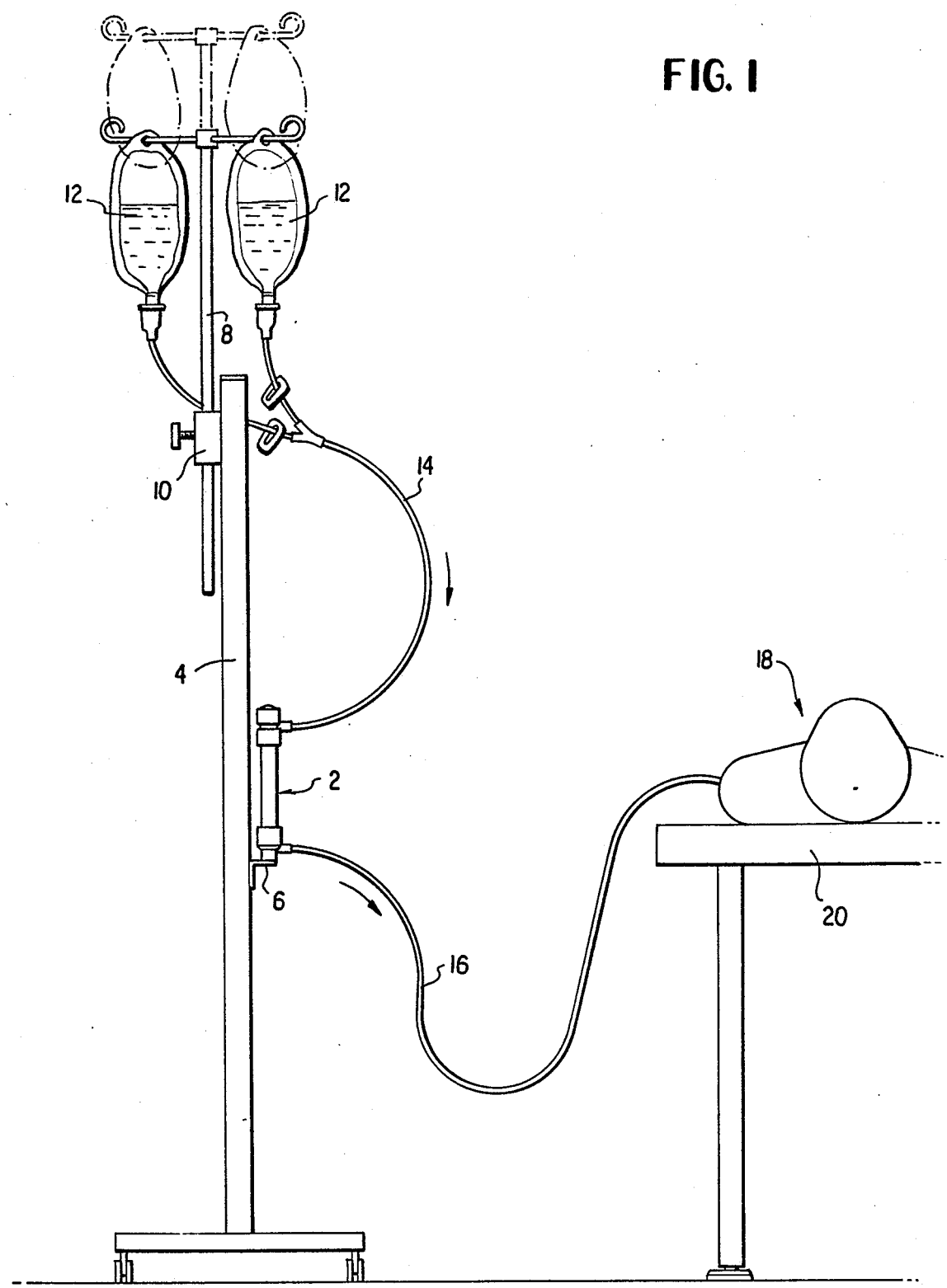
FIG. 1 is a side view of the apparatus of the invention shown in use with a patient.

With reference to FIG. 1, a preferred embodiment of the invention is illustrated. An air-elimination device 2 is attached to a support 4 by a bracket 6. As will be described below, bracket 6 cooperates with the air eliminator 2 to maintain the air eliminator in a vertical orientation. A T-shaped hanger 8 is mounted to support 4 by a clamp 10. Hanger 8 provides support for fluid holding bags 12 which are in turn connected to air elimination device 2 by an inlet tube 14. The outlet of air elimination device 2 is connected to a patient 18 by a tube 16.

Patient 18 is schematically shown resting on a platform 20 which is at a height approximately equal to that of a normal hospital bed.

For proper operation of the air eliminator 2, the fluid bags 12 must be higher than a hydrophobic filter (see FIG. 2) located at the upper end of gas eliminator 2. This provides a fluid pressure head to be exerted on the hydrophobic filter to cause gas which has separated from the fluid to pass to the atmosphere. The height at which bags 12 are held by hanger 8 provides a desired pressure head by any type known in the art, for increasing the flow rate of the fluid, were used, air would pass through the hydrophobic filter even faster. The height of bracket 6 is such that below patient 18 whereby no significant negative pressure is created within the gas eliminator 2, which would cause gas to flow through the hydrophobic filter from the atmosphere into the gas eliminator.

In a preferred embodiment, the gas eliminator outlet is a maximum of 36 inches above the floor. The hanger 8 supports fluid holding bags 12 at a height normally employed to provide a flow of fluid through the force of gravity into patient 18, and this is sufficient to force removed gas outwardly through the hydrophobic membrane of the preferred embodiment.

Figure 2:
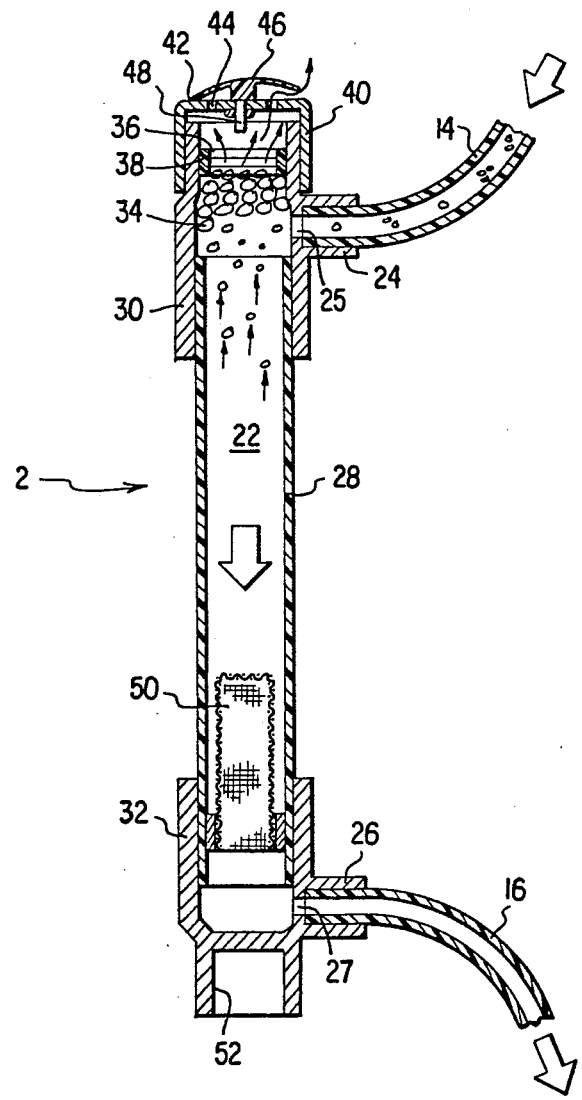
FIG. 2 is longitudinal cross-section of an air-elimination device shown in use in FIG. 1.

With reference to FIG. 2, a longitudinal cross section of the gas eliminator 2 is shown.

A plenum 22 has a fluid inlet 24 and a fluid outlet 26. In the embodiment shown, plenum 22 comprises a cylndrical tube 28 closed by end caps 30 and 32 which are cemented to the tube. These elements may be molded into a single piece if desired.

As fluid flows through tube 14 into plenum 22, gas bubbles 34 will form and naturally separate from the fluid. Generally, the cross-sectional dimensions of plenum 22 are larger than those of the fluid outlet 26 whereby the downward vertical velocity of the fluid through plenum 22 is less than the upward velocity of the air bubbles rising to the surface. In a preferred embodiment tube 28 has an inside diameter of from 0.510 to 0.490 in. with 0.500 being preferred. The diameter of aperture 25 of inlet 24 and aperture 27 of outlet 26 is 0.155 in.

The distance between the inlet and outlet is large enough that bubbles cannot flow directly from the inlet to the outlet, and is preferably larger than 4 inches. In a preferred embodiment, that dimension is 5 to 5½ inches.

The top of plenum 22 is covered by a membrane 36 which is held in a ring 38. Membrane 36 is preferably made of expanded polytetrafluoroethylene (PTFE) which is microporous. The pores are preferably from 0.2 micron to 1.2 microns, and the membrane is laminated to a web of spun-bonded polyester or polypropylene to retain permeability while providing tensile strength.

The surface area and permeability of the membrane must be such that sufficient gas will be vented at pressures less than the pressure required to drive the column of liquid in plenum 22 downwardly to outlet 26.

In a preferred embodiment, a one-way valve 40 is secured to the upper end of air eliminator 2. This valve includes an upper wall 42 with holes 44 therein, for allowing gas which has passed membrane 36 to escape to the atmosphere. A flexible umbrella value 46 is attached to upper wall 42 by a stem 48 and is flexible to allow gas from the plenum to escape through holes 44 but to prevent gas from flowing through holes 44 toward membrane 36.

One-way valve 40 is a safety measure to prevent gas from flowing into plenum 22 through membrane 36, which would happen if patient 18 were too low. For example, if patient 18 were below the gas eliminator 2, a negative pressure could develop in plenum 22, which would tend to draw gas into plenum 22 through membrane 36 in the absence of one-way valve 40. In those instances where it is assured that the relative elevations of patient 18 and gas eliminator 2 will be proper, one-way valve 40 may be eliminated.

A particulate filter 50 may be placed in plenum 22 to remove particles from the fluid. This filter plays no role in gas elimination and is preferably made of nylon or polyester screen.

A cavity 52 at the bottom of air eliminator 2 may be provided for receiving a projection (not shown) on bracket 6. Cooperation of bracket 6 and cavity 52 supports the air eliminator 2 and maintains it in a vertical orientation for proper operation of the device. Other means for orienting and supporting gas eliminator 2 will be apparent to those of skill in the art. For example, a U-shaped bracket may be used to engage a mid-portion of plenum 22.

In operation, gas eliminator 2 is installed as shown in FIG. 1. As the fluid enters the gas eliminator, it begins a downward flow with a reduced velocity. The maximum downward flow rate of the fluid is designed to be less than the upward velocity of the bubbles so that bubbles rise to the uppermost part of the plenum. The bubbles 35 accumulate on the lower surface of membrane 36, which tends to protect membrane 36 and prevent it from being clogged with cellular materials. The pressure required to vent the air bubbles through the hydrophobic membrane 36 is less than the pressure driving the column of fluid downwardly, and gas passes through the membrane to the atmosphere.

Modifications of the preferred embodiment within the scope of the following claims will be apparent to those of skill in the art.

What is claimed is:

1. Apparatus for eliminating a gas from a cellular fluid comprising plenum means and mounting means, said plenum means comprising means for separating said gas from said cellular fluid, said means for separating consisting of a chamber for producing a vertical flow rate in a fluid flowing therethrough adequate to release said gas in the form of bubbles which rise to the top of said chamber when said chamber is vertical, said chamber having a fluid inlet, a fluid outlet below said fluid inlet, and a hydrophobic membrane above said fluid inlet when said chamber is in an operational orientation for freely receiving said bubbles and for passing said gas of said bubbles directly to the atmosphere through said membrane while preventing passage of said fluid, and wherein said mounting means comprises means for engaging support means for supporting said plenum only when said chamber is substantially vertical and for preventing rotating of said chamber about a horizontal axis.

2. Apparatus according to claim 1 wherein said plenum comprises a hollow cylinder and said membrane means comprises a hydrophobic material extending completely across said cylinder.

3. Apparatus according to claim 2 further comprising valve means in communication with said membrane means for venting gas from said plenum passed by said membrane means to the atmosphere and for preventing a flow of air from the atmosphere through said membrane.

4. Apparatus according to claim 3 wherein said hollow cylinder has an inside diameter of about 0.500 inches, said inlet and outlet have inside diameters of about 0.155 inches, and said cylinder has a length of at least 4 inches.

5. Apparatus according to claim 3 further comprising filter means for removing particulates from said fluid.

6. Apparatus according to claim 2 further comprising said support means for supporting said plenum means, said support means comprising means for cooperating with said means for engaging for orienting said chamber substantially vertical.

7. Apparatus according to claim 6 wherein said support means comprises means for holding a container of a physiological fluid a predetermined minimum distance above said plenum means.

8. Apparatus according to claim 7 wherein said predetermined minimum distance is the distance which will provide a pressure head adequate to force said gas through said membrane.

9. Apparatus according to claim 6 wherein said support means engages said mounting means only when said hydrophobic filter is above said inlet.

10. Apparatus according to claim 9 wherein said support means comprises a vertical stud, and said means for engaging comprises a recess.

11. Apparatus according to claim 1 wherein said mounting means is designed to engage said support means only when said hydrophobic filter is above said inlet.

12. A method for eliminating gas from a physiological fluid comprising providing an orientation-dependent means for separating said gas from said fluid, said means for separating comprising chamber means having a hydrophobic membrane at one end, an outlet at an opposite end and an inlet between said membrane and said outlet for allowing said gas to flow upwardly through said fluid only when said chamber means is vertical and means for engaging a support means for supporting said chamber means only when said chamber means is vertical and for preventing rotation of said chamber means about a horizontal axis, providing said means for supporting said chamber means only when said chamber is vertical, and attaching said chamber means to said means for supporting in an orientation wherein said membrane is above said inlet.

13. A method according to claim 12 wherein said means for supporting further comprises means for holding a container of physiological fluid a predetermined minimum distance above said means for separating and further comprising the steps of attaching a said container to said means for holding and placing said container in fluid communication with said means for separating.

14. In combination, gas eliminator means for separating a gas from a fluid and support means for supporting said gas eliminator means, said gas eliminator means comprising plenum means and mounting means, said plenum means consisting of a chamber for producing a vertical flow rate in a fluid flowing therethrough adequate to release said gas in the form of bubbles which rise to the top of said chamber when said chamber is substantially vertical, said chamber having a hydrophobic membrane at one end of said chamber, an outlet at an opposite end of said chamber, and an inlet between said membrane and said outlet, said hydrophobic membrane being for freely receiving said bubbles and for passing said gas directly to the atmosphere, said support means securely engaging and supporting said gas eliminator only when said chamber is substantially vertical and preventing rotation of said gas eliminator about a horizontal axis.

15. A combination according to claim 14 wherein said support means comprises means for holding a container of a physiological fluid above said chamber by a sufficient distance to create a pressure head adequate to force said gas through said membrane.

* * * * *